United States Patent [19]
Zink et al.
[11] Patent Number: 4,668,966
[45] Date of Patent: May 26, 1987

[54] ALIPHATIC BRIDGED CHROMOGENIC BISQUINAZOLINES SUBSTITUTED WITH PHENYLAMINE OR PHENYL-CONTAINING HETEROBICYCLIC RADICALS

[75] Inventors: Rudolf Zink, Therwil; Ian J. Fletcher, Magden, both of Switzerland

[73] Assignee: Ciba-Geigy Corporation, Ardsley, N.Y.

[21] Appl. No.: 721,963

[22] Filed: Apr. 11, 1985

[30] Foreign Application Priority Data

Apr. 18, 1984 [CH] Switzerland ........................ 1950/84

[51] Int. Cl.[4] ........................ B41M 5/16; B41M 5/22; C07D 403/06; C07D 403/12

[52] U.S. Cl. .................................. 346/218; 430/138; 544/74; 544/80; 544/284

[58] Field of Search .......................... 544/284, 74, 80; 346/218; 430/138

[56] References Cited

U.S. PATENT DOCUMENTS

| | | | |
|---|---|---|---|
| 3,340,260 | 9/1967 | Blatter | 544/119 |
| 3,574,210 | 4/1971 | Breuer | 544/293 |
| 3,637,693 | 1/1972 | Oherstedt | 544/283 |
| 3,931,179 | 1/1976 | Simpson | 544/284 |
| 3,998,951 | 12/1976 | Harnish | 544/283 |
| 4,011,323 | 3/1977 | Simpson | 544/284 |
| 4,306,065 | 12/1981 | Chen | 544/293 |
| 4,435,003 | 3/1984 | Fletcher | 428/320.4 |
| 4,480,096 | 10/1984 | Fletcher | 544/289 |
| 4,497,887 | 2/1985 | Watanabe et al. | 430/138 |
| 4,562,449 | 12/1985 | Balli et al. | 346/218 |
| 4,587,538 | 5/1986 | Shanton et al. | 346/218 |

FOREIGN PATENT DOCUMENTS 0033716 1/1981 European Pat. Off. .

*Primary Examiner*—Glennon H. Hollrah
*Assistant Examiner*—James H. Turnipseed
*Attorney, Agent, or Firm*—Edward McC. Roberts; Meredith C. Findlay; Irving M. Fishman

[57] ABSTRACT

The invention relates to bisquinazolines of the formula

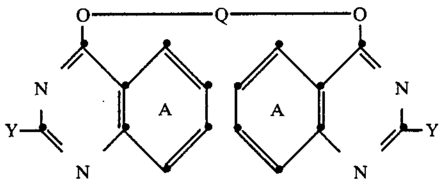

(1)

wherein the ring

A is unsubstituted or substituted by cyano, nitro, halogen, lower alkyl, phenyl, benzyl, lower alkoxy or lower alkoxycarbonyl, Q is an aliphatic radical with a molecular weight of 28 to 450, or is a cycloaliphatic or araliphatic radical, Y is the radical of the formula (2a)

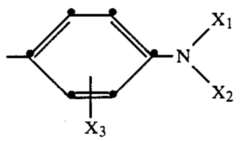

(2a)

or of the formula

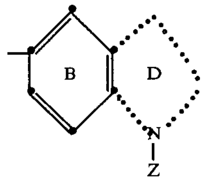

(2b)

wherein B, D, $X_1$, $X_2$, $X_3$ and Z are as hereinafter defined.

These compounds are particularly suitable as colour formers in pressure-sensitive or heat-sensitive recording materials and give strong yellow or orange colours of excellent fastness to light, especially fastness to sublimation.

24 Claims, No Drawings

ALIPHATIC BRIDGED CHROMOGENIC BISQUINAZOLINES SUBSTITUTED WITH PHENYLAMINE OR PHENYL-CONTAINING HETEROBICYCLIC RADICALS

The present invention relates to chromogenic bisquinazolines, to a process for the preparation thereof, and to the use of these compounds as colour formers in pressure-sensitive or heat-sensitive recording materials.

The novel bisquinazolines have the general formula

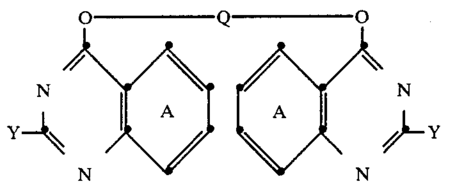

(1)

wherein the ring

A is unsubstituted or substituted by a group selected from cyano, nitro, halogen, lower alkyl, phenyl, benzyl, lower alkoxy and lower alkoxycarbonyl, and Q is an aliphatic radical having a molecular weight in the range from 28 to 450, or is a cycloaliphatic or araliphatic radical containing not more than 10 carbon atoms, Y is the radical of the formula

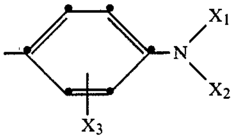

(2a) or

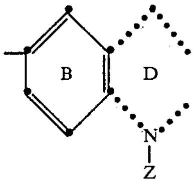

wherein $X_1$ and $X_2$, each independently of the other, are hydrogen, alkyl of not more than 12 carbon atoms, unsubstituted or substituted by a group selected from halogen, hydroxy, cyano and lower alkoxy, or are cycloalkyl, phenyl, benzyl, or phenyl or benzyl, each substituted by a group selected from halogen, nitro, cyano, lower alkyl, lower alkoxy and lower alkoxycarbonyl; or $X_1$ and $X_2$, together with the nitrogen atom to which they are attached, are a 5- or 6-membered, preferably saturated, heterocyclic radical, $X_3$ is hydrogen, halogen, lower alkyl, lower alkoxy or lower alkoxycarbonyl, and Z is hydrogen or alkyl of not more than 8 carbon atoms, unsubstituted or substituted by a group seleted from halogen, cyano and lower alkoxy, or is cycloalkyl or benzyl, and the benzene ring B is unsubstituted or substituted by cyano, halogen, lower alkyl, for example methyl, or lower alkoxy, for example methoxy, and the ring D is a hydrogenated 5- or 6-membered N-heterocycle which may contain a further hetero atom as ring member, for example an oxygen, sulfur or nitrogen atom, and is unsubstituted or C-substituted by one or, depending on the substituents, more members selected from halogen, cyano, hydroxyl, lower alkyl, lower alkoxy, $C_5$–$C_6$cycloalkyl, benzyl and $C_3$–$C_6$alkylene.

In the definitions of the radicals of the bisquinazolines, lower alkyl and alkoxy normally denote those groups or moieties that contain 1 to 5, preferably 1 to 3, carbon atoms. Examples of lower alkyl groups are methyl, ethyl, n-propyl, isopropyl, n-butyl, sec-butyl, tert-butyl or amyl; and lower alkoxy groups are for example methoxy, ethoxy, isopropoxy or tert-butoxy.

An aliphatic radical Q is in particular an alkylene group which is unsubstituted or substituted by halogen atoms, preferably chlorine. The alkylene group can contain from 2 to 8 carbon atoms and may be straight chain or branched. The alkylene group preferably contains 2 to 5 carbon atoms and is, for example, a member selected from $$-CH_2-CH_2-,\ -CH_2-\underset{CH_3}{\underset{|}{CH}}-,\ CH_3-\overset{|}{\underset{CH_3}{\underset{|}{C}}}-\overset{|}{\underset{CH_3}{\underset{|}{C}}}-CH_3,$$

$$-CH_2-\underset{CH_2Cl}{\underset{|}{CH}}-\ ,\ -CH_2CH_2CH_2-,\ -\underset{CH_3}{\underset{|}{CH}}-CH_2CH_2-,$$

$$-CH_2\underset{CH_3}{\underset{|}{CH}}-CH_2-,\ -CH_2CH_2CH_2CH_2-,$$

$$-CH_2-(CH_2)_3-CH_2-,\ -CH_2-\overset{CH_3}{\overset{|}{\underset{CH_3}{\underset{|}{C}}}}-CH_2-,$$

$$-CH_2-(CH_2)_4-CH_2-\ \text{or}\ -CH_2(CH_2)_6-CH_2-.$$

The aliphatic hydrocarbon radical can be interrupted in the chain of atoms by oxygen atoms and is thus the radical of a polyalkylene glycol, for example polyethylene glycol, polypropylene glycol or polybutylene glycol. Further, Q is advantageously the radical of the formula $$-(CH_2CH_2O)_m-CH_2CH_2- \qquad (1a)$$

or $$-(CH_2-\underset{CH_3}{\underset{|}{CHO}})_s CH_2-\underset{CH_3}{\underset{|}{CH}}- \qquad (1b)$$

wherein m is 1 to 9, preferably 1 to 3, and s is 1 to 5, preferably 1 or 2.

Q as a cycloaliphatic radical is for example the 1,2-cyclopentylene group, the 1,2-cyclohexylene group, the 1,3-cyclohexylene group, the 1,4-cyclohexylene group or

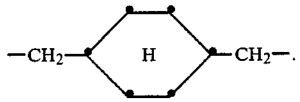

These cycloaliphatic radicals may contain one or two methyl groups.

Q as an araliphatic radical may be for example

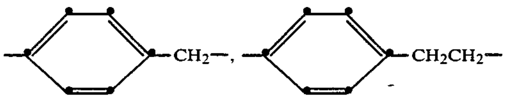

or

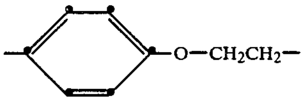

Q is preferably an aliphatic or cycloaliphatic radical, in particular $C_2$–$C_4$alkylene and, most preferably, ethylene.

The ring A is preferably not further substituted. If it does contain further substituents, then these are preferably halogen, lower alkyl or lower alkoxy, for example chlorine, methyl, isopropyl, tert-butyl or methoxy. Each benzene ring may conveniently contain 1 or 2 substituents.

Alkyl groups $X_1$ and $X_2$ may be straight chain or branched. Examples of such alkyl groups are: methyl, ethyl, n-propyl, isopropyl, n-butyl, sec-butyl, amyl, n-hexyl, 2-ethylhexyl, n-octyl, isooctyl or n-dodecyl.

Substituted alkyl groups $X_1$ and $X_2$ are in particular cyanoalkyl, haloalkyl, hydroxyalkyl or alkoxyalkyl, in which the alkyl moieties preferably contain 2 to 4 carbon atoms. Examples of such substituted alkyl groups are: β-cyanoethyl, β-chloroethyl, β-hydroxyethyl, β-methoxyethyl or β-ethoxyethyl.

$X_1$ and $X_2$ as cycloalkyl are, for example, cyclopentyl or, preferably, cyclohexyl. These cycloalkyl radicals may contain one or more $C_1$–$C_4$-alkyl radicals, preferably methyl groups, and preferably contain in all 5 to 10 carbon atoms.

Preferred substituents of the phenyl and benzyl moiety of $X_1$ and $X_2$ are, for example, halogen atoms, cyano, methyl, methoxy or carbomethoxy. Examples of such araliphatic and aromatic radicals are methylbenzyl, chlorobenzyl, cyanophenyl, tolyl, xylyl, chlorophenyl, methoxyphenyl or carbomethoxyphenyl.

A heterocyclic radical $—NX_1X_{12}$ is for example pyrrolidino, piperidino, pipecolino, morpholino, thiomorpholino, or piperazino such as N-methylpiperazino. Preferred heterocyclic radicals $—NX_1X_2$ are pyrrolidino, piperidino or morpholino.

$X_1$ and $X_2$ are each independently of the other preferably lower alkyl, benzyl, phenyl, lower alkylphenyl or lower alkoxyphenyl. $X_3$ is preferably hydrogen, chlorine, methyl, methoxy or ethoxy.

The ring B is preferably unsubstituted. However, it may with advantage contain a methyl group. The ring D is preferably 6-membered and C-substituted in particular by 1, 2 or 3 methyl groups.

Z is preferably lower alkyl, benzyl or β-cyanoethyl.

Preferred bisquinazolines of the formula (1) are those in which Y is a radical of the formula (2a).

Interesting chromogenic bisquinazolines are those of the formula (3)

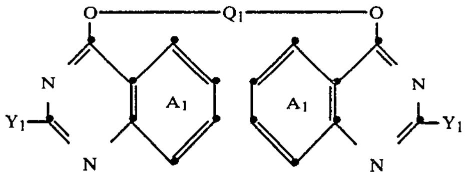

wherein $Q_1$ is a straight chain or branched alkylene radical of 2 to 8, preferably 2 to 5, carbon atoms, or is the $—(CH_2CH_2O)_{m1}—CH_2CH_2—$ radical, $Y_1$ is an aminophenyl radical of the formula (3a)

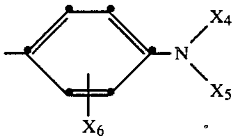

a 5-indolinyl radical of the formula (3b)

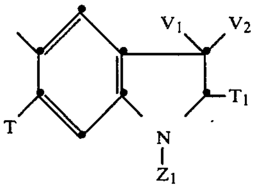

a tetrahydroquinolinyl radical of the formula (3c)

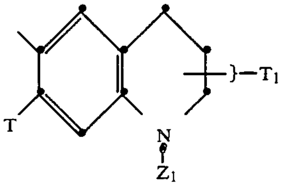

a tetrahydroquinolinyl radical of the formula (3d)

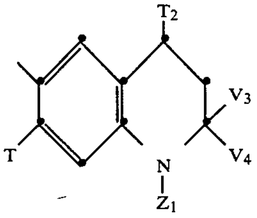

or a benzomorpholino radical of the formula (3e)

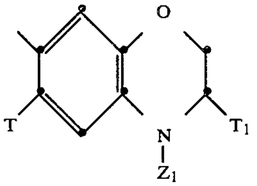

and $m_1$ is 1 to 3.

$X_4$ and $X_5$ are each independently of the other lower alkyl, cyanolower alkyl, benzyl, phenyl, lower alkylphenyl or lower alkoxyphenyl; or $X_4$ and $X_5$, together with the nitrogen atom to which they are attached, are pyrrolidino, piperidino or morpholino, $X_6$ is hydrogen, halogen, lower alkyl or lower alkoxy, $Z_1$ is hydrogen, $C_1$–$C_8$alkyl, $C_2$–$C_6$alkoxyalkyl, β-cyanoethyl or benzyl, T is hydrogen, halogen, lower alkyl, lower alkoxy, $C_1$–$C_4$acylamino, for example acetylamino or propionylamino, or is phenyl, $T_1$ and $T_2$ are each independently of the other hydrogen, halogen, hydroxy, lower alkyl or lower alkoxy, and $V_1$, $V_2$, $V_3$ and $V_4$ are each independently hydrogen, lower alkyl, cycloalkyl or benzyl; or ($V_1$ and $V_2$) or ($V_3$ and $V_4$) are each together alkylene, and and the ring $A_1$ is unsubstituted or substituted by one or two members selected from cyano, halogen, lower alkyl, phenyl and lower alkoxy.

Among the bisquinazolines of formula (3), those compounds are preferred in which $Y_1$ is an aminophenyl radical of the formula (3a). $X_4$ and $X_5$ are lower alkyl or benzyl. $X_6$ is preferably hydrogen. $Q_1$ is preferably $C_2$–$C_4$alkylene and is in particular ethylene or propylene. $Q_1$ is preferably also $—CH_2CH_2—O—CH_2CH_2—$ or the cyclohexylene radical. The ring $A_1$ is preferably unsubstituted.

In the bisquinazolines of the formula (3), wherein $Y_1$ is a radical of the formula (3b), (3c), (3d) or (3e), the N-substituent $Z_1$ is preferably benzyl, β-cyanoethyl, or $C_1$–$C_8$alkyl, e.g. n-octyl, n-butyl, isopropyl or, most preferably, methyl or ethyl.

$Y_1$ is preferably the tetrahydroquinoline radical of the formula (3d). T is preferably hydrogen or methyl. $T_1$ is preferably hydrogen, methyl, hydroxyl or chlorine. $T_2$ is preferably hydrogen, methyl or ethyl. $V_1$ and $V_2$ are preferably hydrogen or methyl; and $V_3$ and $V_4$ are each preferably lower alkyl and, most preferably, are each methyl.

If ($V_1$ and $V_2$) or ($V_3$ and $V_4$) together are alkylene, then they contain preferably 4 or 5 carbon atoms and, together with the carbon atom to which they are attached, form a cyclopentane or cyclohexane ring.

Particularly interesting bisquinazolines are those of the formula

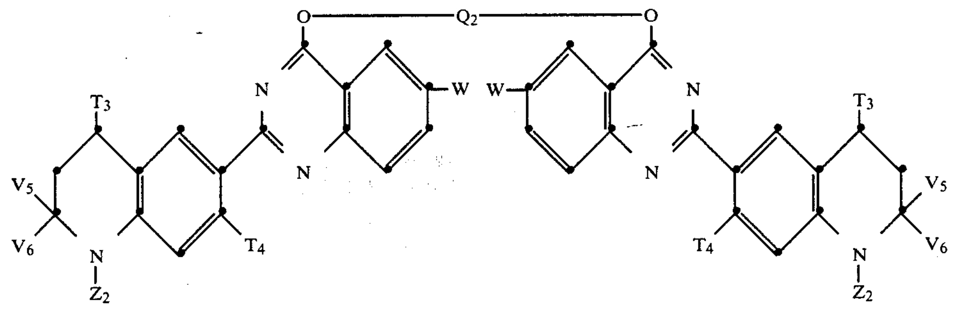

(4)

or, most particularly, those of the formula

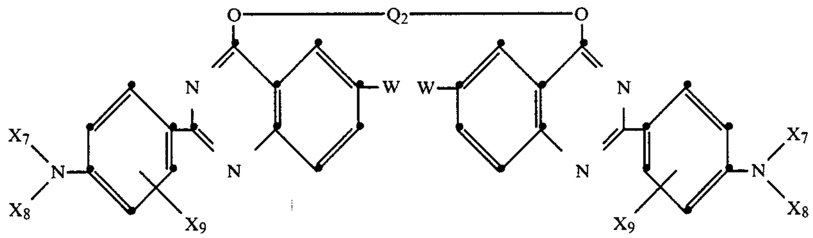

(5)

wherein $Q_2$ is straight chain or branched $C_2$–$C_4$alkylene, $—CH_2CH_2—O—CH_2CH_2—$, $(—CH_2CH_2O—)_2CH_2CH_2—$,

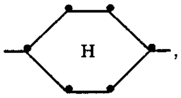, 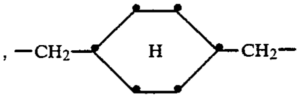 or

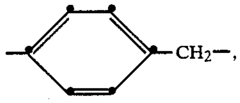, $X_7$ and $X_8$ are each independently of the other lower alkyl or benzyl; or $—NX_7X_8$ is piperidino, $X_9$ is hydrogen, methyl, methoxy or ethoxy, $Z_2$ is $C_1$–$C_8$alkyl, β-cyanoethyl or benzyl, $T_3$, $V_5$ and $V_6$ are each independently lower alkyl, preferably methyl or ethyl, $T_4$ is hydrogen or methyl, and W is halogen, methyl, methoxy or, preferably, hydrogen.

Preferred bisquinazoline compounds are those of the formula (5), wherein $Q_2$ is $C_2$–$C_4$alkylene, preferably propylene or, most preferably, ethylene, or also $—CH_2CH_2—O—CH_2CH_2—$. $X_7$ and $X_8$ are preferably benzyl or, most preferably, lower alkyl. W and $T_4$ are preferably hydrogen. Q is preferably also

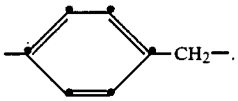

Halogen in connection with the above substituents in formulae (1) to (5) is e.g. fluorine, bromine or, preferably, chlorine.

The bisquinazolines of the formula (1) are prepared by reacting 1 mole of a diol of the formula $$HO-Q-OH \quad (6)$$

wherein Q is as defined, with 2 moles of a 4-haloquinazolin of the formula

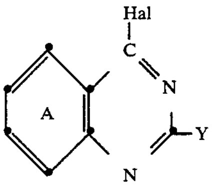

(7)

wherein A and Y have the given meanings and Hal is halogen, for example bromine, fluorine or, preferably, chlorine.

The reaction of the compound of the formula (6) with the compound of formula (7) is conveniently carried out in the presence of an acid acceptor, e.g. an alkali metal hydroxide, alkali metal carbonate or a tertiary nitrogen base, e.g. pyridine or a trialkylamine, and preferably also in the presence of a quaternary ammonium salt, e.g. tetrabutylammonium bromide, optionally in an organic solvent or in an aqueous-organic two-phase medium, and at reflux temperature.

Suitable solvents are for example cycloaliphatic or aromatic hydrocarbons such as cyclohexane, benzene, toluene or xylene; chlorinated hydrocarbons such as chloroform, ethylene chloride or a chlorobenzene, preferably dichlorobenzene; ethers such as diethyl ether or glycol dimethyl ether; cyclic ethers such as dioxan or tetrahydrofuran; and dimethylformamide, diethylformamide, dimethylsulfoxide or acetonitrile.

Diols of the formula (6), which can be employed as starting materials for the reaction with the quinazolines of the formula (7), preferably have the formula $$HO-Q'-OH \quad (8)$$

wherein Q' is $C_2$–$C_8$alkylene, cyclohexylene,

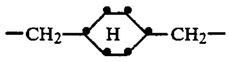 or 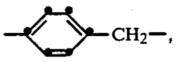, or have the formula $$HO-(-CH_2-CH_2-O)_{n}H \quad (9)$$

wherein n is 1 to 10, preferably 1 to 4.

Representative examples of starting diols of the formula (6) are: ethylene glycol, 1,2- or 1,3-propylene glycol, 1,3-, 1,4- or 2,3-butylene glycol, 2-methyl-1,3-propanediol, 3-chloro-1,2-propanediol, 2,2-dimethyl-1,3-propanediol, neopentyl glycol, 2,3-dimethyl-2,3-butanediol (pinacol), 1,5-pentanediol, 3-methyl-1,5-pentanediol, 2-methyl-2,4-pentanediol, 1,6- or 2,5-hexanediol, 1,8-octanediol, 1,2-, 1,3- or 1,4-cyclohexanediol, cyclohexane-1,4-dimethanol, diethylene glycol, triethylene glycol, tetraethylene glycol, dipropylene glycol, dibutylene glycol, 4-hydroxybenzyl alcohol, 4-hydroxyphenylethanol or 4-hydroxyphenoxyethanol.

The starting materials of the formula (7) can be prepared by reacting e.g. a 2-aminobenzamide of the formula (10)

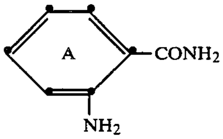

with an aldehyde of the formula $$Y-CHO \quad (11)$$

to give a 1,2,3,4-tetrahydroquinazol-4-one of the formula (12)

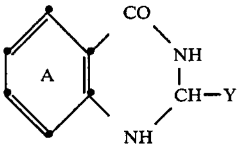

oxidising this compound to a compound of the formula (13)

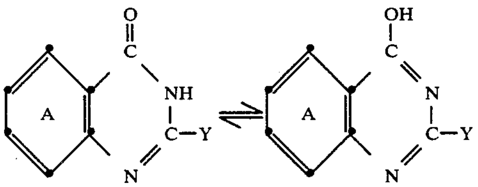

then replacing the hydroxyl group at the heterocyclic ring of the quinazoline system by a halogen atom, e.g. with phosphoroxy chloride in dichlorobenzene or with thionyl chloride in dimethylformamide, to give the starting material of the formula (7). The 4-haloquinazoline can be further used without being isolated.

The oxidation of the reaction products of the formula (12) to the 4-quinazolones of the formula (13) is carried out with oxidising agents. Suitable oxidising agents are e.g. chromates, bichromates, chlorates, chlorites, peroxides, e.g. hydrogen peroxide, manganese dioxide, lead dioxide, molecular oxygen, air, perborates, permanganates, nitrites, chlorine, bromine, bromine and, in particular, chloranil or bisulfites.

The best results with respect to yield and purity of the 4-quinazolones are obtained whth chloranil as preferred oxidising agent. The oxidation with sodium bisulfite affords ecological advantages. Following the procedure described in Synthesis 1981, (1), 35, quinazolones of the formula (13) are obtained in good yield and purity using this oxidising agent.

The 4-haloquinazolines of the formula (7) and 4-quinazolones of the formula (13), and the preparation thereof, are described for example in published European patent application No. 33716.

The bisquinazolines of the formula (1) to (5) are normally colourless or, at most, faintly coloured. When these colour formers are brought into contact preferably with an acid developer, e.g. an electron acceptor, they produce strong yellow or orange shades of excellent light fastness, especially fastness to sublimation. They are therefore also very useful when combined with one or more other known colour formers, for example, 3,3-(bis-aminophenyl)phthalides, 3,3-(bis-indolyl)phthalides, 3-aminophenyl-3-indolylazaphthalides, 3-aminofluoranes, 2,6-diaminofluoranes, leucoauramines, spiropyranes, spirodipyranes, chromenoindoles, chromenopyrazoles, phenoxazines, phenothiazines, monoquinazolines, carbazolylmethanes or other triarylmethaneleuco dyes, to give blue, grey or black colorations.

The bisquinazolines of the formulae (1) to (5) exhibit both on phenolic substrates, and especially on activated clays, an excellent colour intensity and fastness to sublimation and light. They are particularly suitable as rapidly developing colour formers for use in a heat-sensitive, or especially in a pressure-sensitive, recording material which can also be a copying material. They are distinguished by the property that they have excellent solubility in the capsule oils.

A pressure-sensitive material consists, for example, of at least one pair of sheets which contain at least one colour former of the formulae (1) to (5) dissolved in an organic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, zinc nitrate, activated kaolin or any clay, or acidic organic compounds, for example unsubstituted or ring-substituted phenols, salicylic acid or salicylates and their metal salts, or an acidic polymer, for example a phenolic polymer, an alkylphenol acetylene resin, a maleic acid/rosin resin or a partially or completely hydrolysed polymer of maleic acid and styrene, ethylene or vinyl methyl ether, or carboxypolymethylene. Mixtures of these polymers can also be used. Particularly preferred developers are acid clays, zinc salicylates, or the condensation products of p-substituted phenols with formaldehyde. These last mentioned compounds may also contain zinc.

The developers may also be used in admixture with other basically inert or almost inert pigments or with other auxiliaries such as silica gel or UV absorbers, e.g. 2-(2-hydroxyphenyl)-benzotriazoles. Examples of such pigments are: talcum, titanium dioxide, zinc oxide, chalk, clays such as kaolin, as well as organic pigments, e.g. urea/formaldehyde condensates (BET surface area: 2–75 $m^2/g$) or melamine/formaldehyde condensates.

The colour former effects a coloured marking at those points where it comes into contact with the electron acceptor. In order to prevent the colour formers contained in the pressure-sensitive recording material from becoming active prematurely, they are usually separated from the electron acceptor. This separation can conveniently be accomplished by incorporating the colour formers in foamlike, spongelike or honeycomb-like structures. The colour formers are preferably encapsulated in microcapsules, which can normally be ruptured by pressure.

When the capsules are ruptured by pressure, for example with a pencil, the colour former solution is transferred to an adjacent sheet which is coated with an electron acceptor and a coloured area is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. with isopropyl, isobutyl, sec- or tert-butyl) derivative of diphenyl, diphenylalkane, naphthalene or terphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation.

The capsules walls can be formed evenly around the droplets of the colour former solution by coacervation; and the encapsulating material can consist of gelatin and gum arabic, as described e.g. in U.S. Pat. No. 2,800,457. the capsules can also be formed preferably from an aminoplast or a modified aminoplast by polycondensation, as described in British patent specifications Nos. 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (5) can be used for the production of a wide variety of known kinds of pressure-sensitive copying material. The various systems differ substantially from one another in the arrangement of the capsules, of the colour reactants, and of the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethylcellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of the formulae (1) to (5) can also be employed as colour formers in a thermoreactive recording material. This recording material usually contains at least one carrier, one colour former, one electron acceptor, and optionally also a binder, and/or wax.

Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) information can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer.

Another possibility comprises in dispersing both the colour former and the developer in one layer. By means of heat the binder is softened at specific areas and the colour former comes into contact with the developer (electron acceptor) at those points where heat is applied and the desired colour develops at once.

Suitable developers are the same electron acceptors as are used in pressure-sensitive papers. Examples of developers are the clays already mentioned and especially phenolic resins, or also the phenolic compounds described e.g. in German Offenlegungsschrift No. 1 251 348, for example 4-tert-butylphenol, 4-phenylphenol, methylene bis-(2-methylphenyol), 4-hydroxydiphenyl ether, α-naphthol, β-naphthol, methyl 4-hydroxybenzoate, 4-hydroxyacetophenone, 2,2'-dihydroxydiphenyl, 4,4'-isopropylidenediphenol, 4,4'-isopropylidene-bis-(2-methylphenol), 4,4'-bis-(hydroxyphenyl) valeric acid, hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the bisquinazolines and the developer are sparingly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethylcellulose, methyl cellulose, carboxymethylcellulose, polyacrylamide, polyvinyl pyrrolidone, gelatin, starch, or etherified corn starch.

If the colour former and the developer are in two separate layers, it is possible to ue water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose or polyvinyl carbazole. The preferred arrangement, however, is that in which the colour former and the developer are contained in one layer in a water-soluble binder.

The thermoreactive coatings may contain further auxiliaries. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, stearyl amide, phthalic anhydride, metal stearates, dimethyl terephthalate, phthalonitrile or other appropriate fusible products which induce the simultaneous melting of the colour former and the developer. Thermographic recording materials preferably contain waxes, e.g. carnauba wax, montan wax, paraffin wax, polyethylene wax, condensates of higher fatty acid amides and formaldehyde, or condensates of higher fatty acids and ethylenediamine.

The invention is illustrated by the following Examples, in which percentages are by weight, unless otherwise indicated.

EXAMPLE 1

To 29.3 g of the quinazolone of the formula

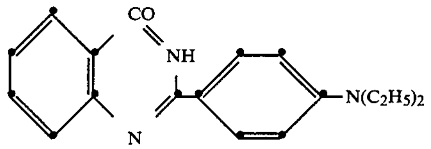

(i)

in 70 g of xylene (mixture of isomers, b.p. 138°-142° C.) are added 16 g of phosphoroxy chloride at 90° C. The reaction mixture is stirred for 1 hour at this temperature to give a dark red solution of the 4-chloro-2-(4'-diethylaminophenyl)quinazoline of the formula

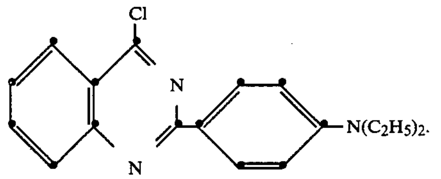

(ii)

This solution is added dropwise to a suspension of 3.1 g of ethylene glycol, 100 g of a 50% solution of sodium hydroxide and 1 g of tetrabutylammonium bromide. The suspension so obtained is stirred for 1 hour under reflux and then 150 ml of water are added at 90° C. The xylene phase is separated and washed repeatedly with hot water, then cooled with stirring. The product is precipitated in crystalline form by addition of 100 g of methanol at 35° C. The precipitate is isolated by filtration at 15°-20° C., washed with methanol and water and dried, affording 22 g of a bisquinazoline compound of the formula

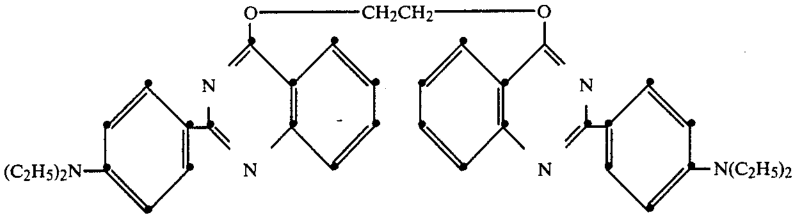

(21)

with a melting point of 189°-190° C.; $\epsilon=81300$ at 438 nm, determined in 95% acetic acid.

On acid clay this colour former develops a strong yellow colour of good lightfastness and excellent fastness to sublimation. The maximum of reflectance of this bisquinazoline compound is 464 nm on paper coated with acid clay.

Following the procedure of Example 1, the bisquinazolines of the formula

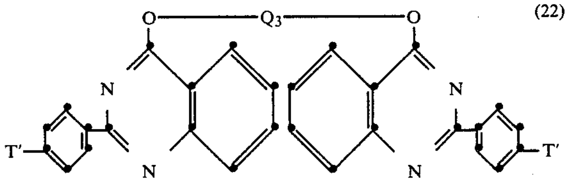

(22)

are obtained using the starting materials listed in the following table.

TABLE

| Example | T' | $Q_3$ | m.p. °C. | Colour on acid clay |
|---|---|---|---|---|
| 2 | $-N(C_2H_5)_2$ | $-CH_2CH_2CH_2-$ | 160-163 | yellow |
| 3 | $-N(C_2H_5)_2$ | $-(CH_2)_4-$ | 190-191 | yellow |
| 4 | $-N(C_2H_5)_2$ | 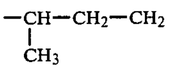 | 70-75 | yellow |
| 5 | $-N(C_2H_5)_2$ | $-(CH_2)_5-$ | 71-74 | yellow |
| 6 | $-N(C_2H_5)_2$ | $-CH_2CH_2OCH_2CH_2-$ | 69-75 | yellow |
| 7 | $-N(C_2H_5)_2$ | $-(CH_2CH_2O)_2CH_2CH_2-$ | 151-155 | yellow |
| 8 | $-N(C_2H_5)_2$ | 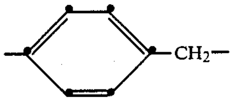 | 119-121 | yellow |
| 9 | 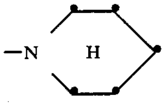 | $-CH_2-CH_2-$ | | yellow |
| 10 | 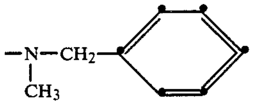 | $-CH_2-CH_2-$ | | yellow |
| 11 | $-N(n\text{-}C_3H_7)_2$ | $-CH_2CH_2-$ | | yellow |
| 12 | $-N(C_2H_5)_2$ | 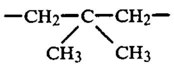 | 175-177 | yellow |
| 13 | $-N(C_2H_5)_2$ | 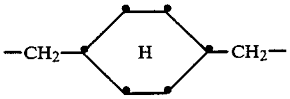 | 220-222 | yellow |
| 14 | $-N(C_2H_5)_2$ | 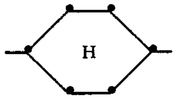 | 100-110 | yellow |

EXAMPLE 15

17 g of the quinazolone of the formula

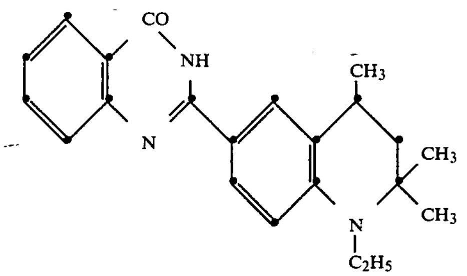

are suspended at 90° C. in 50 g of toluene. Chlorination is effected by adding 8 g of phosphoroxy chloride over 30 minutes at 90° C. The red reaction solution of the compound of the formula

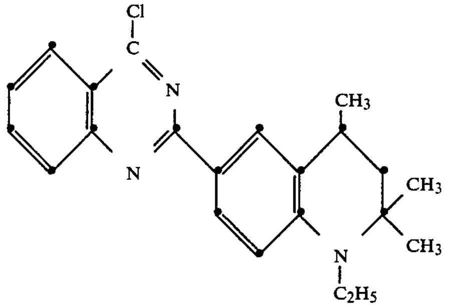

is stirred for 1 hour at 85°-90° C. Then the solution is added dropwise to a suspension of 1.6 g of ethylene glycol, 30 g of a 50% solution of sodium hydroxide and 1 g of tetrabutylammonium chloride. The emulsion is stirred for 2 hours at 90°-95° C. and then the toluene phase is separated and washed with water. The product is precipitated in crystalline form by addition of 80 g of methanol at 40° C. The precipitate is isolated by filtration, washed with methanol and dried, affording 10.1 g of a virtually colourless bisquinazoline of the formula

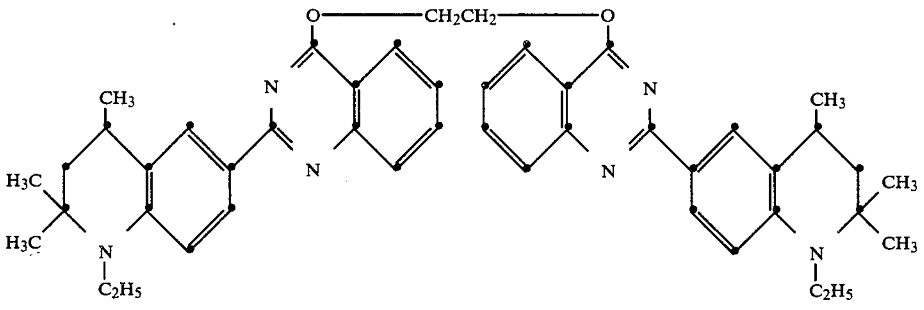

Recrystallisation from a 7:3 mixture of toluene/isopropyl alcohol affords the pure product with a melting point of 228°-229° C. On acid clay, this colour former develops a yellow colour of good light-fastness. In addition, this colour former has excellent fastness to sublimation.

EXAMPLE 16

Preparation of a pressure-sensitive copying paper

A solution of 3 g of the bisquinazoline of the formula (21) in 80 g of partially hydrogenated terphenyl and 17 g of kerosene are microencapsulated by coacervation in a manner known per se with gelatin and gum arabic. The microcapsules are mixed with starch solution and coated on a sheet of paper. The face of a second sheet of paper is coated with acid-activated bentonite as colour developer. The first sheet and the sheet coated with the developer are laid on top of each other with the coated sides face to face. Pressure is exerted on the first sheet by writing by hand or type-writer and a strong yellow copy of excellent fastness to sublimation and light develops immediately on the sheet coated with the developer.

Corresponding strong yellow copies which are fast to sublimation and light are also obtained by using any of the other colour formers of formula (22) in Examples 2 to 15.

EXAMPLE 17

Following the procedure as described in Example 16, but replacing the bisquinazoline of the formula (21) by a mixture of the following composition:

1.4 g of 3,3-bis-(4'-dimethylaminophenyl)-6-dimethylaminophthalide,
1.0 g of N-butylcarbazol-3-yl-bis-(4'-N-methyl-N-phenylaminophenyl)methane,
0.6 g of the bisquinazoline of the formula (21) and
0.5 g of 3,3-bis-(N-n-octyl-2'-methylindol-3'-yl)phthalide, there is obtained a pressure-sensitive recording material which gives a strong and lightfast black copy by writing by hand or typewriter.

EXAMPLE 18

1 g of the bisquinazoline of the formula (21) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m$^2$ with a mixture consisting of 1 part of an amide wax, 1 part of a stearin wax and 1 part of zinc chloride. Pressure is exerted on the top sheet by hand or typewriter and a strong yellow copy which is fast to sublimation and light develops immediately on the sheet coated with the colour former.

EXAMPLE 19

Preparation of a heat-sensitive recording material

In a ball mill, 32 g of 4,4'-isopropylidenediphenol (bisphenol A), 3.8 g of the distearylamide of ethylenediamine, 39 g of kaolin, 20 g of an 88% hydrolysed polyvinyl alcohol and 500 ml of water are ground to particle size of about 5 μm. In a second ball mill, 6 g of the compound of the formula (21), 3 g of a 88% hydrolysed polyvinyl alcohol and 60 ml of water are ground to a particle size of about 3 μm.

Both dispersions are mixed and applied to paper to a dry coating weight of 5.5 $g/m^2$. A strong yellow colour of excellent fastness to light and sublimation is produced by contacting the paper with a heated ball-point pen.

Strong lightfast yellow colours can also be obtained by using any of the other colour formers of the formula (22) indicated in Examples 2 to 15.

EXAMPLE 20

In a ball mill, 2.7 g of the bisquinazoline of the formula (21), 24 g of N-phenyl-N'-(1-hydroxy-2,2,2-trichloroethyl)urea, 16 g of stearylamide, 59 g of an 88% hydrolysed polyvinyl alcohol and 58 ml of water are ground to a particle size of 2–5 μm. This suspension is applied to a sheet of paper to a dry coating weight of 5.5 $g/m^2$.

A strong yellow colour which is fast to sublimation and light is obtained by contacting the paper with a heated ball-point pen.

What is claimed is:

1. A chromogenic bisquinazoline of the formula

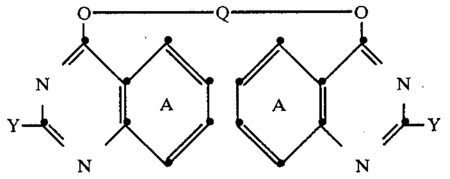

wherein the ring

A is unsubstituted or substituted by a group selected from nitro, halogen, lower alkyl, phenyl, benzyl, lower alkoxy and lower alkoxycarbonyl;

Q is an alkylene or heteroalkylene radical having 2 to 8 carbon atoms, a radical of a polyalkylene glycol having a molecular weight in the range of from 28 to 450, or a radical of the formula $$-(CH_2CH_2O)_m CH_2CH_2- \text{ or } -(CH_2-\underset{CH_3}{CH}O)_s CH_2-\underset{CH_3}{CH}-,$$

wherein m is 1 to 9 and s is 1 to 5, or is a cycloaliphatic or araliphatic radical having not more than 10 carbon atoms;

Y is the radical of the formula

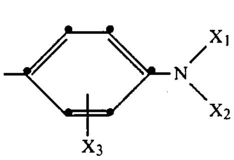

or

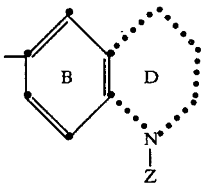

wherein $X_1$ and $X_2$, each independently of the other, is hydrogen, alkyl of not more than 12 carbon atoms, unsubstituted or substituted by a group selected from halogen, hydroxy, cyano and lower alkoxy, or are cycloalkyl having 5 to 10 carbon atoms, phenyl, benzyl, or phenyl or benzyl, each substituted by a group selected from halogen, nitro, cyano, lower alkyl, lower alkoxy and lower alkoxycarbonyl; or $X_1$ and $X_2$, together with the nitrogen atom to which they are attached, are a 5- or 6-member N-heterocyclic radical or a heterocyclic radical which has, in addition to nitrogen, at least one additional hetero atom selected from the group consisting of nitrogen, oxygen and sulfur;

$X_3$ is hydrogen, halogen, lower alkyl, lower alkoxy or lower alkoxycarbonyl, and Z is hydrogen or alkyl of not more than 8 carbon atoms, unsubstituted or substituted by a member selected from the group consisting of halogen, cyano and lower alkoxy, and the benzene ring B is unsubstituted or substituted by cyano, halogen, lower alkyl or lower alkoxy, and the ring D is a hydrogenated 5- or 6-membered N-heterocyclic ring system which is unsubstituted or C-substituted by one or more of the same or different members selected from the group consisting of halogen, cyano, hydroxyl, lower alkyl, lower alkoxy, $C_5$–$C_6$cycloalkyl, benzyl and $C_3$–$C_6$alkylene.

2. A bisquinazoline according to claim 1, wherein Y in formula (1) is the radical of the formula (2a).

3. A bisquinazoline according to claim 2, wherein $X_1$ and $X_2$ in formula (2a) are each independently of the other lower alkyl, benzyl, phenyl, lower alkylphenyl or lower alkoxyphenyl.

4. A bisquinazoline according to claim 1, wherein Y in formula (1) is the radical of the formula (2b), wherein Z is lower alkyl, benzyl or β-cyanoethyl.

5. A bisquinazoline according to claim 1, wherein Y in formula (1) is the radical of the formula (2b), wherein the ring D is 6-membered.

6. A bisquinazoline according to claim 1, wherein Q in formula (1) is $C_2$–$C_5$alkylene.

7. A bisquinazoline according to claim 1, of the formula (3)

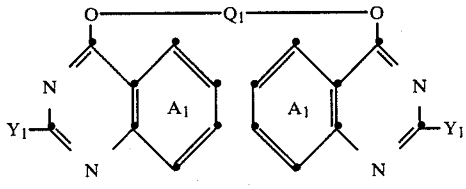

wherein $Q_l$ is a straight chain or branched alkylene radical of 2 to 8, carbon atoms, or is the $—(CH_2CH_2O)_{m1}—CH_2CH_2—$ radical, $Y_1$ is an aminophenyl radical of the formula

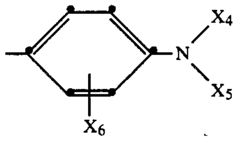
(3a)

or a 5-indolinyl radical of the formula

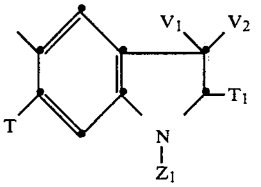
(3b)

a tetrahydroquinolinyl radical of the formula

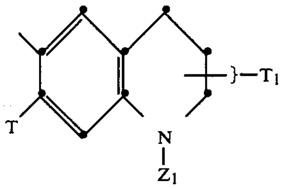
(3c)

a tetrahydroquinolinyl radical of the formula

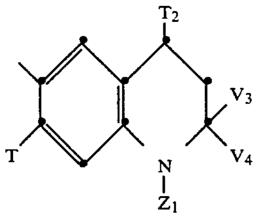
(3d)

or a benzomorpholino radical of the formula

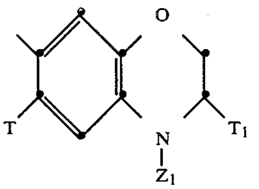
(3e)

wherein $m_1$ is 1 to 3, $X_4$ and $X_5$ are each independently of the other lower alkyl, cyanolower alkyl, benzyl, phenyl, lower alkylphenyl or lower alkoxyphenyl; or $X_4$ and $X_5$, together with the nitrogen atom to which they are attached, are pyrrolidino, piperidino or morpholino, $X_6$ is hydrogen, halogen, lower alkyl or lower alkoxy, $Z_1$ is hydrogen, $C_1$–$C_8$alkyl, $C_2$–$C_6$alkoxyalkyl, β-cyanoethyl or benzyl, T is hydrogen, halogen, lower alkyl, lower alkoxy, $C_1$–$C_4$acylamino or phenyl, $T_1$ and $T_2$ are each independently of the other hydrogen, halogen, hydroxy, lower alkyl or lower alkoxy, and $V_1$, $V_2$, $V_3$ and $V_4$ are each independently hydrogen, lower alkyl, cycloalkyl or benzyl; or ($V_1$ and $V_2$) or ($V_3$ and $V_4$) are each together alkylene, and and the ring $A_1$ is unsubstituted or substituted by one or two members selected from cyano, halogen, lower alkyl, phenyl and lower alkoxy.

8. A bisquinazoline according to claim 7, wherein $Y_1$ in formula (3) is a radical of the formula (3a).

9. A bisquinazoline according to claim 8, wherein in formula (3a) $X_4$ and $X_5$ are lower alkyl or benzyl and $X_6$ is hydrogen.

10. A bisquinazoline according to claim 7, wherein $Q_1$ in formula (3) is $C_2$–$C_5$alkylene.

11. A bisquinazoline according to claim 7, wherein the ring $A_1$ in formula (3) is unsubstituted.

12. A bisquinazoline according to claim 7, wherein $Y_1$ in formula (3) is the radical of the formula (3d).

13. A bisquinazoline of the formula

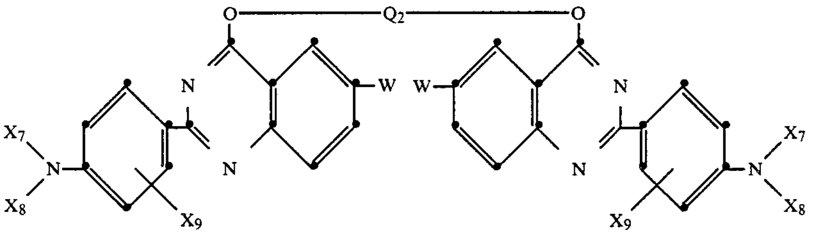
(5)

wherein $Q_2$ is straight chain or branched $C_2$–$C_4$alkylene, $—CH_2CH_2—O—CH_2CH_2—$, $(—CH_2CH_2O—)_2CH_2CH_2—$,

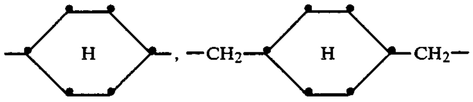
or

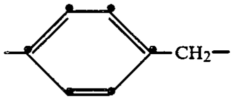

$X_7$ and $X_8$ are lower alkyl or benzyl, or $—NX_7X_8$ is piperidino, $X_9$ is hydrogen, methyl, methoxy or ethoxy, and W is hydrogen, halogen, methyl or methoxy.

14. A bisquinazoline according to claim 13, wherein in formula (5) $Q_2$ is $C_2$–$C_4$alkylene or $—CH_2C-$ $H_2$—O—$CH_2CH_2$—, $X_7$ and $X_8$ are lower alkyl, and $X_9$ and W are hydrogen.

15. A bisquinazoline according to claim 13, wherein $Q_2$ in formula (5) is

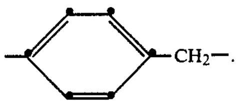

16. A bisquinazoline according to claim 13, wherein $Q_2$ in formula (5) is ethylene or propylene.

17. A bisquinazoline according to claim 1, of the formula

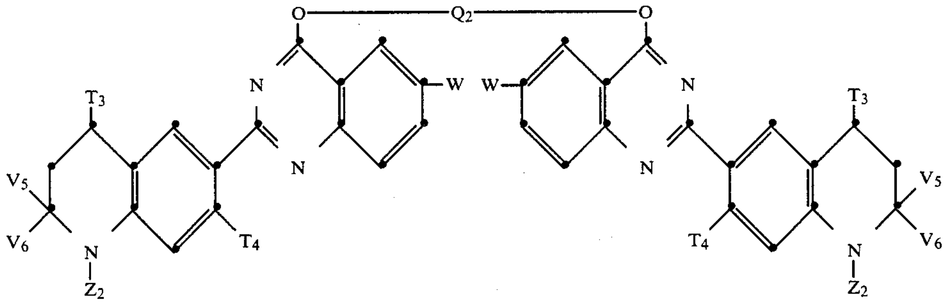

(4)

wherein $Q_2$ is straight chain or branched $C_2$-$C_4$alkylene or —$CH_2$—$CH_2$—O—$CH_2$—$CH_2$—, $Z_2$ is $C_1$-$C_8$alkyl, β-cyanoethyl or benzyl, $T_3$, $V_5$ and $V_6$ are each independently lower alkyl, $T_4$ is hydrogen or methyl, and W is hydrogen, halogen, methyl or methoxy.

18. A bisquinazoline according to claim 16, wherein in formula (4) $Z_2$ is lower alkyl, $T_3$, $V_5$ and $V_6$ are methyl, and $T_4$ and W are hydrogen.

19. A pressure-sensitive or heat-sensitive recording material which comprises a support which contains, or has coated thereon as color former, at least one bisquinazoline of the formula as indicated in claim 1.

20. The pressure-sensitive recording material of claim 19, wherein the bisquinazoline is dissolved in an organic solvent, and which recording material further comprises at least one solid electron acceptor.

21. The pressure-sensitive recording material of claim 20, wherein the bisquinazoline is encapsulated in microcapsules.

22. The pressure-sensitive recording material of claim 21, wherein the encapsulated bisquinazoline is present in the form of a layer on the back of a transfer sheet and the electron acceptor is present in the form of a layer on the face of a receiving sheet.

23. The pressure-sensitive recording material of claim 19, which comprises the bisquinazoline together with one or more other color formers.

24. The heat-sensitive recording material of claim 19, which comprises in at least one layer, at least one color former, at least one electron acceptor and at least one binder.

* * * * *